United States Patent [19]
Leunbach

[11] Patent Number: 5,322,065
[45] Date of Patent: * Jun. 21, 1994

[54] STABLE FREE RADICAL CONTAINING CONTRAST MEDIA

[75] Inventor: Ib Leunbach, Strandvej, Denmark

[73] Assignee: Nycomed Innovation AB, Malmo, Sweden

[*] Notice: The portion of the term of this patent subsequent to Jan. 15, 2008 has been disclaimed.

[21] Appl. No.: 613,471

[22] PCT Filed: Jul. 17, 1989

[86] PCT No.: PCT/EP89/00832

§ 371 Date: Oct. 29, 1990

§ 102(e) Date: Oct. 29, 1990

[87] PCT Pub. No.: WO90/00904

PCT Pub. Date: Feb. 8, 1990

[30] Foreign Application Priority Data

Jul. 19, 1988 [GB] United Kingdom ............... 8817137

[51] Int. Cl.$^5$ .............................................. A61B 5/05
[52] U.S. Cl. .................................................. 128/653.4
[58] Field of Search ........................ 128/653.2, 653.4; 324/307, 309; 424/1.1, 9

[56] References Cited

U.S. PATENT DOCUMENTS

| | | | |
|---|---|---|---|
| 4,516,075 | 5/1985 | Moran | 324/309 |
| 4,615,879 | 10/1986 | Runge et al. | |
| 4,719,425 | 1/1988 | Ettinger | 128/731 |
| 4,893,627 | 1/1990 | Kehayias et al. | 128/653.4 |
| 4,984,573 | 1/1991 | Leunbach | 128/653.4 |
| 5,042,488 | 8/1991 | Ackerman | 128/654 |

FOREIGN PATENT DOCUMENTS

| | | |
|---|---|---|
| 1230114 | 12/1987 | Canada. |
| 0071564 | 2/1983 | European Pat. Off.. |
| 0296833 | 12/1988 | European Pat. Off.. |
| 7134802 | 4/1973 | France. |
| 2154857 | 5/1973 | France. |
| WO85/02772 | 7/1985 | PCT Int'l Appl.. |
| WO85/04330 | 10/1985 | PCT Int'l Appl.. |
| WO87/01594 | 3/1987 | PCT Int'l Appl.. |
| 8705222 | 9/1987 | PCT Int'l Appl.. |

OTHER PUBLICATIONS

Alcock et al., *Tetrahedron*, 33, 2969–2980, 1977.
Golding et al., *Synthesis*, 7, 462–463, 1975.
Chignell, *The Application of Electron Spin Resonance and Spin-Labeling in Biochemistry and Pharmacology*, pp. 1–6.
Barbarin et al., *Chemical Abstracts*, 89:171456v, 1978.
Beth, *Chemical Abstracts*, 92:124350h, 1980.
R. Chiarelli et A. Rossat, "Nitroxydes-LVI, Synthesis de Radicoux Nitroydes Deuteries" Tetrahedron, vol. 29, 1973, pp. 3639–3647.
David Lurie et al., "Proton-Electron Double Magnetic Resonance Imaging of Free Radical Solutions", Journal of Magnetic Resonance, vol. 76, 1988, pp. 366–370.
Eriksson et al., "Pharmacokinetics in the Rat and the Dog of a Nonionic Nitroxide Contrast Agent for MRI", Jour. of Pharm. Science, vol. 77, No. 2, Feb. 1988, pp. 97–103.
F. Barbarin et al., "Electron Paramagnetic Resonance: Study of the Macroscopic and Microscopic Orientation of the Ostropic and Nematic Phases of EBBA Using a Deuterated Nitroxid Radical Probe", Chem. Abs., vol. 89, No. 20, Nov. 13, 1978 p. 532.
A. H. Beth, "Advantages of Deuterium Modification of Nitroxide Spin Labels for Biological EPR Studies", Chem. Abs., vol. 92, No. 15, Apr. 14, 1980 p. 304.

Primary Examiner—Lee S. Cohen
Assistant Examiner—Samuel Gilbert
Attorney, Agent, or Firm—Bacon & Thomas

[57] ABSTRACT

The present invention relates to a method of generating a magnetic resonance image of a sample comprising introducing into the sample a physiologically tolerable deuterated stable free radical, exposing the sample to first and second radiations of frequencies selected respectively to excite nuclear spin transitions in selected nuclei in the sample and to excite electron spin resonance transitions of the free radical coupled to nuclear spin transitions of at least some of the nuclei, detecting free induction decay signals from the sample, and generating a magnetic resonance image from these signals.

3 Claims, 2 Drawing Sheets

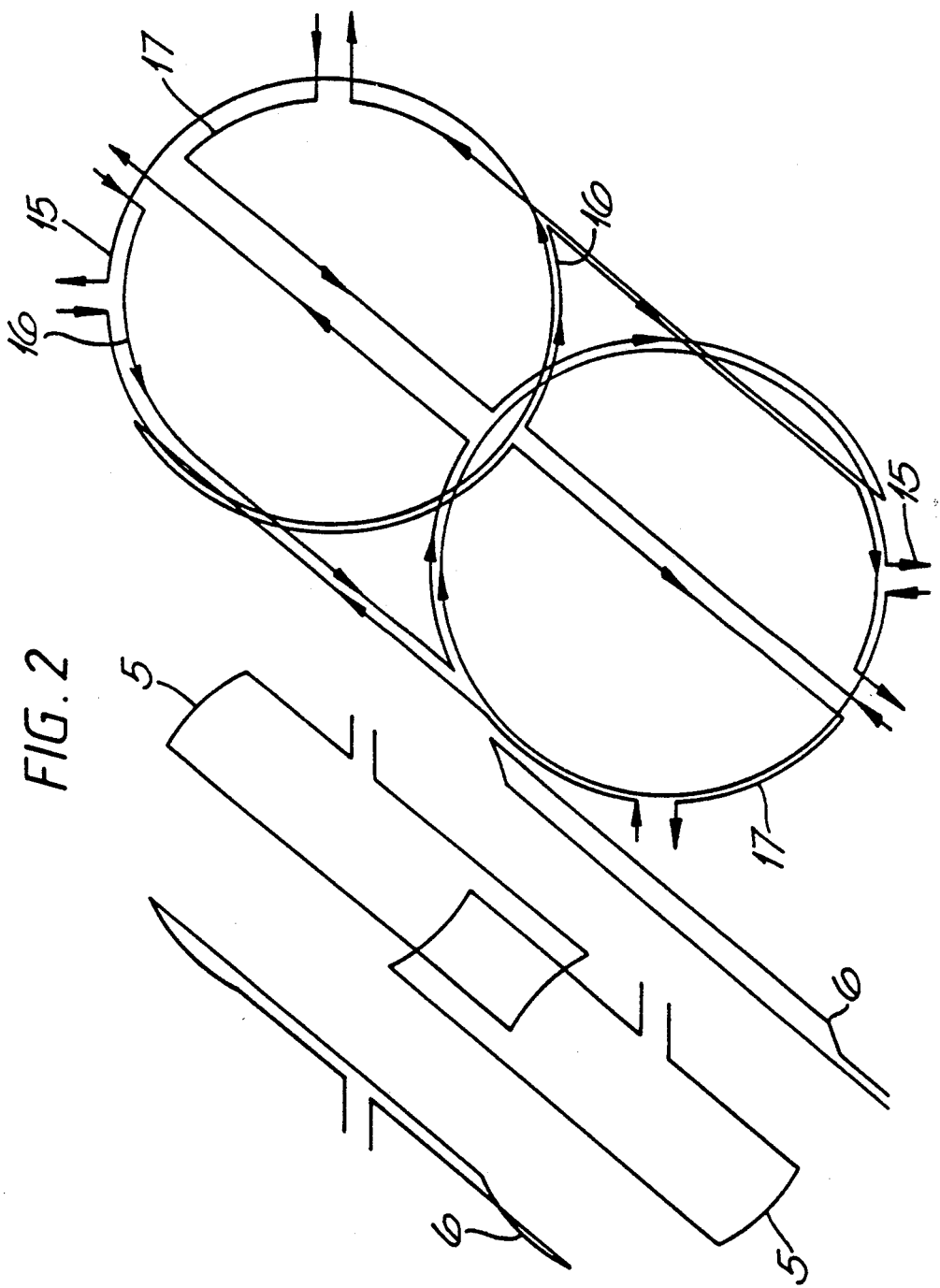

STABLE FREE RADICAL CONTAINING CONTRAST MEDIA

The present invention relates to paramagnetic materials for use in magnetic resonance imaging (MRI), and in particular to media containing deuterated stable free radicals and the use of deuterated free radicals for the manufacture of such contrast media.

MRI is a diagnostic technique that has become particularly attractive to physicians as it is non-invasive and does not involve exposing the patient under study to potentially harmful radiation, such as for example the X-radiation of conventional radiography.

This technique however suffers from several serious draw-backs, including in particular the expense of manufacture and operation of the MRI apparatus, the relatively long scanning time required to produce an image of acceptable spatial resolution, and the problem of achieving contrast in the magnetic resonance (MR) images between tissue types having the same or closely similar imaging parameters, for example in order to cause a tissue abnormality to show up clearly in the images.

The expense of manufacture and operation of an MRI apparatus is closely associated with the field strength that the primary magnet in the apparatus is required to generate in order to produce images of acceptable spatial resolution within an acceptable time (the image acquisition time). In general, magnets capable of generating field strengths of 0.1 to 2 T have been used and image acquisition times are commonly of the order of 10–30 minutes. For relatively low field strengths of up to 0.15 T, resistive magnets (generally adjacent coaxial metal coils) may be used but the energy requirement (and as a result the heat generation) of such resistive magnets is very high. Thus a 0.1 T magnet will require about 30 kW electric power. For higher fields, superconducting magnets are conventionally used. The selection of the appropriate magnetic field strength involves balancing various factors; thus higher field results in a better signal/noise (S/N) ratio and hence better spatial resolution at a given S/N value, but also in greater manufacturing and operating expense and in poorer tissue contrast. There is therefore a demand for MRI apparatus and techniques capable of achieving improvements in S/N ratio, especially if such apparatus would enable lower field magnets to be used without undue loss in spatial resolution.

The long image acquisition times generally result from the need to perform a large number (e.g. 64–1024) of pulse and detection sequences in order to generate a single image and in the need to all the sample under study to reequilibrate between each sequence.

The degeneracy of the spin states of nuclei with non-zero spin, e.g. $^1H$, $^{13}C$, $^{19}F$, etc., is lost when such nuclei are placed within a magnetic field and transitions between the ground and excited spin states can be excited by the application of radiation of the frequency ($\omega_o$) corresponding to energy difference E of the transition (i.e. $\hbar \omega_o = E$). This frequency is termed the Larmor frequency and is proportional to the strength of the applied field. As there is an energy difference between the spin states, when the spin system is at equilibrium the population distribution between ground and excited spin states is a Boltzmann distribution and there is a relative overpopulation of the ground state resulting in the spin system as a whole possessing a net magnetic moment in the field direction. This is referred to as a longitudinal magnetization. At equilibrium the components of the magnetic moments of the individual non-zero spin nuclei in the plane perpendicular to the field direction are randomized and the spin system as a whole has no net magnetic moment in this plane, i.e. it has no tranverse magnetization.

If the spin system is then exposed to a relatively low intensity oscillating magnetic field perpendicular to the main field produced by radiation at the Larmor frequency, generally radiofrequency (RF) radiation, transitions between ground and excited spin states occur. If the exposure is for a relatively short duration then the resultant magnitudes of the longitudinal and transverse magnetizations of the spin system are functions of the exposure duration which oscillate about zero at the Larmor frequency and are 90° out of phase with each other. Thus, from equilibrium, a pulse of duration $(2n+1)\pi/2\omega_o$ (a so-called 90° pulse when n is even and a 270° pulse when n is odd) leaves the system with maximum transverse magnetization (of magnitude proportional to the initial longitudinal magnetization at equilibrium) and no longitudinal magnetization, a pulse of duration $(2n+1)\pi/\omega_o$ (a 180° pulse) leaves the system with inverted longitudinal magnetization and inverted transverse magnetization (and hence from equilibrium no transverse magnetization), etc.

When the pulse is terminated, the oscillating magnetic field produced by any resulting net transverse magnetization can induce an oscillating electrical signal (of angular frequency $\omega_o$) in a detector coil having its axis arranged perpendicular to the main field direction. For this purpose the transmitter used to emit the pulse can also be used as a detector.

Induced nuclear magnetic resonance signals, hereinafter termed free induction decay (FID) signals, have an amplitude proportional to the transverse magnetization (and hence generally to the original population difference between ground and excited spin states).

If the nuclei of the spin system experienced an entirely uniform magnetic field, the FID signal would decay due to spin-spin interactions at a rate with a characteristic time of $T_2$, the transverse or spin-spin relaxation time. However, due to local field inhomogeneities, the nuclei within the spin system will have a spread of Larmor frequencies and decay of transverse magnetization is more rapid, having a characteristic time of $T_2^*$ where $1/T_2^* = 1/T_2 + 1/T_{inh}$, $T_{inh}$ representing the contribution due to field inhomogeneities. $T_2$ itself can be determined using spin-echo imaging in which, after the decay of the FID signal (usually following a 90° pulse) the system is exposed to a 180° pulse and an "echo" signal is generated, the decay in the amplitude of the echo being governed primarily by $T_2$ as, with the inversion of the transverse magnetization for the individual nuclei, the field inhomogeneities referred to above cause tranverse magnetization to build up to a maximum at time TE/2 after the 180° pulse where the time between the previous maximum transverse magnetization and the 180° pulse is also TE/2.

To generate different images, different pulse and FID detection sequences are used. Perhaps the simplest is saturation recovery (SR) where the FID signal is determined after a single 90° initiating pulse. The signal strength is dependent upon the magnitude of the longitudinal magnetization before the pulse, and hence on the nuclear density and the extent to which the system reequilibrates in the time (TR) between successive initiating pulses. In spin-echo imaging, for example multiple-echo imaging, the pulse and detection sequence may be: initiating 90° pulse (at time 0), FID detection (following the initiating pulse), 180° pulse (at time TE/2), detection of 1st echo (at time TE), 180° pulse (at time 3TE/2), detection of 2nd echo (at time 2TE)..., initiating pulse for the next sequence (at time TR), etc. In this technique, a TR is selected which is sufficient for a reasonable reequilibration to occur in the period between successive initiating pulses.

As is explained further below in connection with the example of two dimensional Fourier transformation (2DFT) image generation, in order to generate a single image with adequate spatial resolution, it is necessary to perform a large number (e.g. 64–1024) of separate pulse and detection sequences. Since TR has in principle to be large with respect to $T_1$, the characteristic time for relaxation of the excited system towards the equilibrium Boltzmann distribution between ground and excited spin states, to permit longitudinal magnetization to build up between successive pulse sequences so as to avoid the FID signal strength decaying in successive pulse sequences, the total image acqusition time is generally relatively large. Thus, for example, TR may conventionally be of the order of seconds and the image acquisition time may be of the order of 10–30 minutes.

Certain so-called fast imaging (FI) techniques may be used to accelerate reequilibration and so reduce image acquisition time; however they inherently result in a reduction in the S/N ratio and/or contrast hence in poorer image quality. The FI technique involves for example exciting the spin system with a less than 90° pulse and thus the difference between ground and excited spin state populations is only reduced rather than eliminated (as with a 90° pulse) or inverted and so reattainment of equilibrium is more rapid. Nevertheless, the transverse magnetization generated by the less than 90° pulse is less than that for a 90° pulse and so FID signal strength and thus S/N ratio and the spatial resolution in the final image are reduced.

The long image acquisition time in conventional MRI thus significantly detracts from the attractiveness of MRI for mass or routine diagnostics screening and for all forms of diagnostic imaging where it is necessary to build up a three-dimensional image by imaging successive adjacent sections through the patient.

The third problem mentioned above, that of achieving adequate image contrast between different tissue types, has been addressed in a variety of ways. Using different pulse and detection sequences and by manipulation of the acquired data, MRI can be used to generate a variety of different images, for example saturation recovery (SR), inversion recovery (IR), spin echo (SE), nuclear (usually proton) density, longitudinal relaxation time ($T_1$) and transverse relaxation time ($T_2$) images. Tissues or tissue abnormalities that have poor contrast in one such image often have improved contrast in another. Alternatively, imaging parameters (nuclear density, $T_1$ and $T_2$) for tissues of interest may be altered by administration of a contrast agent. Thus many proposals have been made for the administration of magnetically responsive materials to patients under study (see for example EP-A-71564 (Schering), U.S. Pat. No. 4615879 (Runge), WO-A-85/02772 (Schröder) and WO-A-85/04330 (Jacobsen)). Where such materials, generally referred to as MRI contrast agents, are paramagnetic (for example gadolinium oxalate as suggested by Runge) they produce a significant reduction in the $T_1$ of the water protons in the zones into which they are administered or at which they congregate, and where the materials are ferromagnetic or superparamagnetic (e.g. as suggested by Schröder and Jacobsen) they produce a significant reduction in the $T_2$ of the water protons, in either case resulting in enhanced (positive or negative) contrast in the magnetic resonance (MR) images of such zones.

The contrast enhancement achievable by such agents is limited by a number of factors. Thus such contrast agents cannot move the MRI signal intensity ($I_s$) for any tissue beyond the maximum ($I_1$) and minimum ($I_0$) intensities achievable for that tissue using the same imaging technique (e.g. IR, SR, SE, etc.) in the absence of the contrast agent: thus if "contrast effect" is defined as $(I_s-I_0)/(I_1-I_0)$, contrast agents can serve to alter the "contrast effect" of a tissue within the range of 0–1. However to achieve contrast improvement an adequate quantity of the contrast agent must be administered to the subject, either directly to the body site of interest or in such a way that the natural operation of the body will bring the contrast agent to that body site.

Utilisation of the spin transition coupling phenomenon known in conventional nmr spectroscopy as the Overhauser effect to amplify the Boltzmann population difference due to relaxation of the nuclear spin system producing the MR image by exciting a coupled esr transition in a paramagnetic species in the sample being imaged, generally a human or animal subject has been proposed by us in EP-A-296833.

Our new technique for generating a magnetic resonance image of a sample, hereinafter termed electron spin resonance enhanced magnetic resonance imaging or ESREMRI comprises exposing said sample to a first radiation of a frequency selected to excite nuclear spin transitions in selected nuclei in said sample and detecting free induction decay signals from said sample and is characterised in that it further comprises exposing said sample to a second radiation of a frequency selected to excite electron spin transitions coupled to nuclear spin transitions of at least some of said nuclei.

The MRI apparatus for use in this technique requires a second radiation source for generating the radiation capable of stimulating such an esr transition as well as the first radiation source for generating the radiation used to stimulate the nuclear spin transition. In general, at the magnetic fields that would normally be used with such apparatus, the first and second radiation sources, will be radiofrequency (RF) and microwave (MW) sources respectively and accordingly the first and second radiation sources may be referred to herein as RF and MW sources. It must be appreciated however that the first and second radiations may lie at frequencies outside the ranges conventionally understood as being RF and MW frequencies and in particular that lower frequencies than those conventionally considered to be RF or MW may be utilised.

The MRI apparatus for ESREMRI thus generally comprises a first radiation source capable of emitting a first radiation of a frequency selected to excite nuclear spin transitions in selected nuclei in a sample being imaged and means for detecting free induction decay signals from said selected nuclei, and a second radiation source capable of emitting a second radiation of a frequency selected to excite electron spin transitions coupled to the nuclear spin transitions of at least some of said selected nuclei.

In ESREMRI the sample is exposed to the second radiation for at least part of each RF pulse sequence, e.g. during at least part of the period between the initial pulses of adjacent said sequences. Preferably exposure to the second radiation will be for some, the major part or all of the period during which no magnetic field gradient is imposed on the sample. Conveniently therefore the second radiation may be applied following FID signal determination in each pulse sequence.

It will be appreciated that for certain imaging techniques, particularly saturation recovery (SR) each "pulse sequence" may only involve one pulse of the first radiation while in other MR imaging techniques each pulse sequence may involve several pulses of the first radiation.

The magnetic resonance (MR) image of the sample can be generated in the conventional manner from the detected FID signals. In particular it is not necessary to detect comparative signals from the sample while this is not exposed to the second radiation. Thus generally the apparatus of the invention will comprise means, generally a computer, for transforming the detected FID signals into MR images, these means being arranged to generate such images using only signals detected following emission of both first and second radiations by the radiation sources.

In conventional nmr spectroscopy, it has long been known that if a sample comprising a paramagnetic species and a species containing non-zero spin nuclei, for example sodium dissolved in ammonia, is placed in a strong magnetic field and an esr transition of the paramagnetic species (sodium) is saturated, then peaks in the nmr spectrum of the other species can be very strongly enhanced due to coupling between the electron and nuclear spin transitions. The effect has been termed the Overhauser effect, or dynamic nuclear polarization as exciting the esr transition drives a nuclear spin system at equilibrium towards a new equilibrium distribution with a relatively higher excited state population. In ESREMRI, this effect is operated not as in conventional spectroscopy simply to generate a strong peak in an nmr spectrum but instead to amplify population difference due to relaxation of an excited nuclear spin system.

The amplified population difference may be utilized beneficially in a number of different ways.

Thus to achieve the same S/N ratio and as a result the same spatial resolution, a lower strength main magnetic field (e.g. a lower power and thus more economic primary magnet) and/or a shorter sequence repetition period TR (and hence a shorter image acquisition time) may be used. Alternatively, with no reduction or lesser reductions in main field strength an increase in signal strength (corresponding to a contrast effect of greater than 1) can be obtained, the maximum increase in signal strength being obtained when TR is selected to permit the spin system to reach the new equilibrium between the pulse sequences.

Where only a portion of the nuclei whose spin transitions produce the FID signal (hereinafter the "resonating nuclei") couple with the unpaired electrons of the paramagnetic species, for example due to low concentration or non-uniform distribution of the paramagnetic species in the volume being imaged, contrast enhancement in the image in ESREMRI will also result - thus the FID signal from the resonating nuclei coupling with the unpaired electrons will be enhanced relative to the signals from the noncoupling nuclei. Where the paramagnetic species is either naturally abundant in specific tissues only or is administered in a contrast agent so as to congregate in such tissues, the operation of the invention will therefore allow generation of images in which the contrast enhancement of these tissues is high. It should be noted however that where the power level of the second radiation or the concentration of the paramagnetic material is particularly low it is possible for MR image intensity to be reduced rather than enhanced. Even in such cases however the modified contrast achieved in the resulting MR images may be of interest.

As mentioned above, the paramagnetic substance possessing the esr transition which couples with the nmr transition of the resonating nuclei either may be naturally present within the sample or may be administered thereto in a contrast medium. The present invention is concerned with the case where a paramagnetic species is administered in a contrast medium.

The contrast enhancement achievable using ESREMRI is dependent upon the particular paramagnetic material whose esr transition is stimulated by the second radiation and it is an objective of the invention to provide contrast media particularly suitable for use in ESREMRI.

We have found that one characteristic of the paramagnetic material that is of special importance is the linewidth in its esr spectrum of the line corresponding to the transition that is stimulated by the second radiation and we have found that materials which are at least partially deuterated are more suited for use as ESREMRI contrast agents than their fully protonated analogues.

Thus in one aspect the invention provides the use of a physiologically tolerable deuterated stable free radical for the manufacture of a contrast medium for use in ESREMRI.

In a further aspect the invention provides a method of generating a magnetic resonance image of a sample, said method comprising exposing said sample to a first radiation of a frequency selected to excite nuclear spin transitions in selected nuclei in said sample and detecting free induction decay signals from said sample, characterised in that said method further comprises introducing into said sample a physiologically tolerable deuterated stable free radical and exposing said sample to a second radiation of a frequency selected to excite electron spin transitions of said free radical coupled to nuclear spin transitions of at least some of said nuclei.

The esr linewidth is important as, for efficient amplification of the nuclear spin population difference, the second radiation should be such as to maintain the electron spin system in an excited state, preferably at or near saturation. However, in in vivo imaging it is desirable to minimize the exposure of the patient to the second radiation (generally MW) in order to avoid unwanted heating effects and it is therefore desirable to select an esr transition with long transverse and longitudinal relaxation times, $T_{2e}$ and $T_{1e}$, to allow saturation of the transition to be achieved without undue heating of the sample. Since the line widths of esr transitions in the esr spectrum are proportional to $T_{2e}^{-1}$, the bandwidth required for the second radiation that is used to saturate the esr transition will be smaller where the transition corresponds to a narrow line in the esr spectrum and a long transverse relaxation time is therefore desirable. Similarly since the second radiation absorption required to maintain the (at least partial) saturation is higher for a shorter $T_{1e}$, a long longitudinal relaxation time is desirable for the deuterated stable free radical.

Particularly preferably, the deuterated stable free radical, the substance possessing the esr transition excited by the second radiation, will have an esr spectrum consisting of a single narrow line or a set of closely adjacent narrow lines (for example resulting from hyperfine splitting of a single transition under the effect of neighbouring non-zero spin nuclei within the structure of the paramagnetic substance). Where the esr spectrum contains a reasonably small number of lines it will, as discussed below, be possible simultaneously to excite many or all of the corresponding transitions.

Conventional paramagnetic MRI contrast agents, such as the gadolinium compounds (e.g. Gd-DTPA) suggested by Schering (EP-A-71564), have large spectral linewidths and could not generally be selected since they are highly likely to require unacceptable microwave heating of the sample in order to achieve any significant amplification of the FID signal.

Generally therefore the deuterated stable free radical should preferably have a stimulable esr transition having a line width (i.e. full width at half maximum in the absorbtion spectrum) of the order of $2 \times 10^{-4}$ Tesla or less, especially $10^{-4}$ Tesla or less, preferably $7 \times 10^{-5}$ Tesla or less, particularly preferably $5 \times 10^{-5}$ Tesla or less, especially preferably $10^{-5}$ Tesla or less, and more especially preferably 5 microTesla or less. If the esr spectrum contains a plurality of lines it is furthermore preferred that the total number of these lines be small, for example 2-10, preferably 2 or 3, and/or that the lines or a majority thereof should be separated by not more than about 30 MHz at the operating field of the MRI apparatus in order that several or all of the corresponding esr transitions may be excited.

It will be appreciated that where references are made herein to the limits for esr linewidths these will be the linewidths at imaging conditions, e.g. at the imaged sites. Particularly preferably however the linewidth criteria will be satisfied at the local concentration limits mentioned below.

In general, to avoid hyperfine splitting, the deuterated stable free radical will most desirably contain as few as possible non-zero spin nuclei other than deuterium nuclei, or will contain non-zero spin nuclei other than deuterium only at positions remote from the paramagnetic centre. Conveniently, the molecule may have the atoms near to the paramagnetic centre predominantly selected from zero nuclear spin isotopes or from elements for which the natural abundance of non-zero spin nuclear isotopes is low. Such selection may include elements in which the natural abundance of spin=$\frac{1}{2}$ nuclei is low and isotopes such as $^{14}N$, $^{2}H$, $^{12}C$, $^{32}S$, $^{14}Si$ and $^{16}O$ may for example be used to build up the molecular structure adjacent to the location of the unpaired electron. Alternatively, radicals having nuclei which give rise to hyperfine splitting of the esr transition but with very small coupling constants may be considered.

One particularly interesting group of stable free radicals for use according to the invention are the deuterated nitroxide stable free radicals of which several have been suggested in the literature for use as spin labels. Certain of these compounds are readily available commercially, for example from Merck Sharpe & Dohme. The deuterated nitroxide stable free radicals are of particular interest as the toxicities and pharmacokinetics of their protonated analogues have been studied and show the compounds to be suitable for in vivo MRI and as the esr line widths, especially for compounds in which the atoms adjacent to the NÖ moiety are fully substituted (i.e. carry no protons), are adequately small at the concentrations required to give contrast enhancement.

Where the stable free raicals are only partially deuterated, it is especially preferred that the hydrogens at those sites where $^1H$ would cause the greatest, or indeed any significant, reduction in the $T_{1e}$ or $T_{2e}$ values for the unpaired electron should be $^2H$.

The deuterated radicals used according to the invention preferably have deuterium atoms in place of protons within 3, preferably 4 and especially preferably 5 or more, bonds of the paramagnetic centre, e.g. the oxygen of an NÖ moiety. More especially the radicals are preferably perdeuterated; however where radicals contain labile hydrogens, e.g. acid, amine or alcohol hydrogens, these may preferably be $^1H$ and compounds containing hydrogens distant from the paramagnetic centre which are $^1H$ may also be used to advantage.

As the deuterated nitroxide stable free radicals, there may conveniently be used cyclic nitroxides wherein the NÖ moiety occurs in a 5 to 7-membered saturated or ethylenically unsaturated ring with the ring positions adjacent to it being occupied by doubly substituted carbon atoms and with one of the remaining ring positions being occupied by a carbon, oxygen or sulphur atom and the remaining ring positions being occupied by carbon atoms. Alternatively there may be used as the deuterated nitroxide stable free radicals compounds in which the NÖ moiety occurs in a chain where the adjacent chain atoms are carbon and are not bound to any protons.

Preferred nitroxides may be represented by the formula (I)

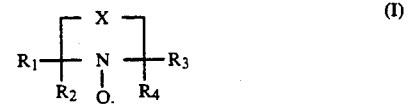

wherein $R_1$ to $R_4$ may represent deuterium or $C_{1-4}$ alkyl or hydroxyalkyl groups and $R_1$ may also represent carboxy substituted $C_{1-10}$ alkyl groups and $R_2$ may also represent a $C_{5-20}$ alkyl group or a carboxy substituted $C_{1-20}$ alkyl group, or $R_1$ and $R_3$ may together represent an alkylene or alkenylene group having up to 4, especially preferably up to 3, carbon atoms and X represents an optionally substituted, saturated or ethylenically unsaturated bridging group having 2 to 4 atoms in the backbone of the bridge one of the backbone atoms being carbon, oxygen or sulphur and the remaining backbone atoms being carbon, with the proviso that one or more of $R_1$ to $R_4$ and X comprises at least one deuterium, preferably any carbon-bound hydrogen within three, and especially preferably within 4, bonds of the nitroxyl nitrogen being a deuterium atom.

In formula I, the moieties $CR_1R_2$ and $CR_3R_4$ are preferably the same. Particularly preferably, $R_1$ to $R_4$ are the same, and it is especially preferred that $R_1$ and $R_4$ should all be perdeuterated methyl groups.

In formula I the optional substitution on X, which preferably is an optionally mono-unsaturated $C_{2-3}$ chain, may for example take the form of halogen atoms or oxo, amino, carboxyl, hydroxy or alkyl groups or combinations or derivatives thereof such as for example amide, ester, ether or N-attached heterocyclic, e.g. 2,5-dioxo-pyrrolidino, groups. Many examples of substituted X groups are described in the literature mentioned below.

The nitroxide molecule may if desired be bound to a further substance, such as for example a sugar, polysaccharide, protein or lipid or to other biomolecules, for example to enhance the blood pooling effect or the tissue- or organ- targetting ability of the nitroxide stable free radical.

In the method and use of the invention there may particularly conveniently be used deuterated, e.g. partially deuterated or perdeuterated, analogues of the protonated nitroxide stable free radicals described below.

Thus for example CA-A-1230114 (Schering) describes nitroxide stable free radicals (for use as MRI contrast agents) of formula II

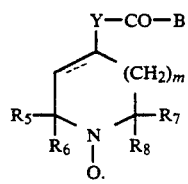

(II)

wherein B is a protein, sugar or lipid residue or a group $—NR_9R_{10}$ ==== is a double or single bond Y is $—(CH_2)_n—$ or if ==== is a single bond also $—NH\,CO—(CH_2)_n—$, n is a number from 0 to 4, m is a number from 0 to 2, $R_9$ and $R_{10}$ are hydrogen or alkyl optionally substituted by hydroxy, acyloxy or alkylidenedioxy (both $R_9$ and $R_{10}$ however cannot simultaneously be hydrogen or unsubstituted alkyl), $R_5$ and $R_7$ are alkyl and $R_6$ and $R_8$ are optionally hydroxy substituted alkyl.

Furthermore, WO87/05222 (MRI Inc.) describes nitroxide stable free radicals (again for use as MRI contrast agents) of formula III

(III)

(when $R_{11}$ to $R_{14}$ are each optionally hydroxy substituted $C_{1-4}$ alkyl, A is $C_{2-4}$ alkylene or alkenylene, $—CH_2—O—CH_2—$ or $—CH_2—S—CH_2—$ and $R_{15}$ is a group $—E—COOM$ where E is $C_{1-8}$ alkylene and M is $NH_4$, Na or K or $R_{15}$ is $—N(Alk)_3^+$, $Hal^-$ where Hal is a halogen atom and Alk is $C_{1-8}$ alkyl optionally substituted by hydroxy or esterified hydroxy), of formula IV

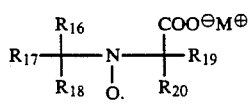

(IV)

(wherein M is as defined above, $R_{16}$, $R_{17}$ and $R_{18}$ are alkyl, cycloalkyl, heterocyclic aliphatic, carbocyclic aryl or heterocyclic aryl and $R_{19}$ and $R_{20}$ are carbocyclic or heterocyclic aryl) and of formula V

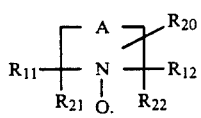

(V)

(wherein $R_{11}$, $R_{12}$, $R_{20}$ and A are as defined above and $R_{21}$ and $R_{22}$ are $—(C_{1-8}\,\text{alkylene})—R_{23}$ where $R_{23}$ is hydrogen, $R_{15}$, $NH_2$, $NHR_{15}$ or $NR_{11}R_{12}$ and $R_{15}$ is as defined above).

Still further nitroxide stable free radicals for use as MRI contrast agents are disclosed in WO87/01594 (Amersham International PLC) and in the references cited therein. The nitroxides disclosed by Amersham are bound, optionally through the agency of linker molecules, to polysaccharides such as dextran, starch and cellulose.

A nitroxide stable free radical of formula VI

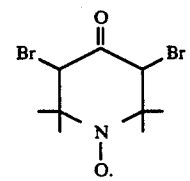

(VI)

is disclosed by Alcock et al in Tetrahedron 33 (1977) 2969-2980.

Nitroxide stable free radicals of formula VII

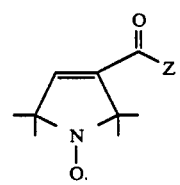

(VII)

(wherein Z is a hydroxyl, ethoxy or a substituted amino group) are disclosed by Golding et al. in Synthesis 7 (1975) 462-463.

Nitroxide stable free radicals of formulae VIII and IX

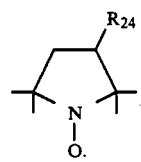

(VIII)

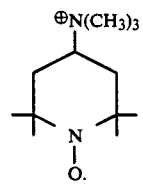

(IX)

(wherein $R_{24}$ is COOH or CONHCH(CH$_2$OH)-CHOHCH$_2$OH) and their pharmacokinetics are discussed by Eriksson et al. in J. Pharm. Sci. 77 (1988) 97-103.

Moreover, nitroxide stable free radicals are discussed generally by C. F. Chignell in "The Application of Electron Spin Resonance and Spin-labelling in Biochemistry and Pharmacology", pages 1 to 6, a publication which indicates at page 6 that the following nitroxide stable free radicals are commercially available from Aldrich:

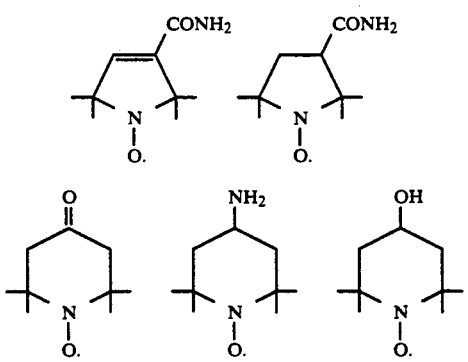

The synthesis of various deuterated nitroxide stable free radicals is described by Chiarelli et al. in Tetrahedron 29:3639-3647 (1973).

Other paramagnetic materials, the use of which may be contemplated, include deuterated, e.g. partially deuterated or perdeuterated analogues of the nitroxides exemplified in our copending European patent application mentioned above or of 3,5-dichloro-2,4,6-tri(hydroxyalkoxy or tri(hydroxyalkyl)silyl)-phenoxy radicals and di(tri(hydroxyalkyl)silanyl)cyclobutadienoquinones, in the latter cases the hydroxyalkyl moieties conveniently containing from 2 to 4 carbon atoms and being for example 2-hydroxyethyl, 2,3-dihydroxypropyl or 3,4-dihydroxybutyl groups.

Certain of the deuterated free radicals useful according to the present invention are novel compounds per se and in further aspects the present invention provides such novel compounds and compositions thereof with physiologically tolerable carriers or excipients. The novel compounds may be prepared using deuterated starting materials by methods analogous to those used for their protonated analogues.

The contrast medium manufactured or used according to the invention may contain, besides the deuterated paramagnetic material, formulation aids such as are conventional for therapeutic and diagnostic compositions in human or veterinary medicine. Thus the media may for example include solubilizing agents, emulsifiers, viscosity enhancers, buffers, etc. The media may be in forms suitable for parenteral (e.g. intravenous) or enteral (e.g. oral) application, for example for application directly into body cavities having external escape ducts (such as the digestive tract, the bladder and the uterus), or for injection or infusion into the cardiovascular system. However, solutions, suspensions and dispersions in physiologically tolerable media will generally be preferred.

For use in in vivo diagnostic imaging, the contrast medium, which preferably will be substantially isotonic, may conveniently be administered at a concentration sufficient to yield a 1 micromolar to 10 mM concentration of the paramagnetic substance at the image zone; however the precise concentration and dosage will of course depend upon a range of factors such as toxicity, the organ targetting ability of the contrast agent, and administration route. The optimum concentration for the paramagnetic substance represents a balance between various factors. In general, operating with a primary magnet generating a 0.02 T field, optimum concentrations have been found to lie in the range 0.1 to 100 mM, especially 1 to 10 mM, more especially 2 to 5 mM. Compositions for intravenous administration preferably will contain the paramagnetic material at concentrations of 10 to 1000 mM, especially preferably 50 to 500 mM. For ionic materials the concentration will particularly preferably be in the range 50-200 mM, especially 140 to 160 mM and for non-ionic materials 200-400 nM, especially 290-330 mM. For imaging of the urinary tract or the renal system however compositions may perhaps be used having concentrations of for example 10-100 mM for ionic or 20 to 200 mM for non-ionic materials. Moreover for bolus injection, the concentration may conveniently be 0.1 to 100 mM, preferably 5 to 25 mM, and especially preferably 6-15 mM.

In a still further aspect the invention provides a contrast medium comprising a physiologically tolerable deuterated nitroxide stable free radical at a concentration of from 10 to 1000 mM in a sterile physiologically tolerable liquid carrier, said nitroxide having an electron spin resonance transition with a linewidth of $10^{-4}$ Tesla or less.

The nitroxides in the contrast medium of the invention will preferably exhibit esr linewidths of less than $10^{-4}$ Tesla especially preferably less than $10^{-5}$ Tesla at concentrations of up to 10 mM, especially at 1 or 2 mM.

As mentioned above, the first and second radiations will generally be RF and MW respectively and the radiation sources thus preferably are RF and MW sources.

The first radiation source is preferably provided with means for adjusting the pulse timing and duration so that the desired imaging technique (e.g. S R, IR, SE, FI, etc.) may be chosen and so that the pulse sequence repetition rate 1/TR may be selected to increase or reduce image acquisition time or to determine $T_1$, $T_2$ or nuclear (usually proton) density.

The first radiation source is also preferably provided with means for adjusting the central frequency, bandwidth, and intensity of the first radiation pulses.

In MRI, the radiation pulse which excites the resonating nuclei is applied while the sample is in a magnetic field conventionally with a field gradient in one direction (e.g. the Z direction). The central frequency and bandwidth of the nuclei exciting pulse together with the Z direction field gradient during the exciting pulse serve to define the position along the Z axis and the thickness in the Z direction of the slice perpendicular to the Z axis containing nuclei whose spin transitions are excited by that pulse. Thus, for example, Fourier transformation of a square wave pulse of central frequency $V_0$ would show such a pulse to contain a range of frequencies centered about $V_0$ and each corresponding to the Larmor frequency of resonating nuclei in a particular XY plane along the Z axis. Thus by providing the apparatus with means for adjusting or selecting the central frequency and bandwidth of the first radiation, the section through the sample (the image zone) and of course the isotopic nature and chemical environment-of the resonating nuclei may be selected.

The second radiation source may be a continuous wave (CW) transmitter or alternatively may be arranged to emit pulses or trains of pulses of the second radiation.

As with the resonating nuclei, the Larmor frequency of the unpaired electron coupling with the resonating nuclei is also dependent on the local magnetic field and not only will the esr transition have a finite linewidth in the esr spectrum, but that spectrum will generally also show some fine structure, i.e. splitting due to the fields generated by non-zero spin nuclei in the paramagnetic material.

To achieve full benefit of the amplified FID signal of the nuclear spin system and to minimize the dosage of the contrast agent (if required), it is therefore beneficial to excite and preferably saturate the electron spin system using a range of frequencies matched to the frequencies of all or most of the peaks in the esr spectrum. This can be done by use of a second radiation source emitting a band of frequencies (e.g. in pulse trains) or by use of two or more sources emitting at different frequencies.

To achieve the desired frequency spread in the second radiation, it may be desirable to use pulses of relatively short duration (hereinafter "micropulses"), for example of the order of nano or microseconds, and to optimize the amplified population difference of the nuclear spin system by keeping the esr transition at or near saturation it may thus be desirable to arrange the second radiation source to emit a train of micropulses, the adjacent micropulses being so spaced as not to permit serious longitudinal relaxation of the electron spin system in the periods between the micropulses.

Alternatively, by providing a decoupling means comprising a third radiation source capable of exciting spin transitions in certain nuclei (other than the resonating nuclei) the number of peaks in the esr spectrum or the linewidth of a broad peak may be reduced. Thus multiple peaks in the esr spectrum of the unpaired electron can arise from coupling between the spins of the electron and nearby non-zero spin nuclei (the transition splitting nuclei) in the same molecule. Where the transition splitting nuclei are not the resonating nuclei for the MRI procedure (for example where they are of different isotopic nature or, if they are of the same isotopic nature, where their chemical shifts are such that their Larmor frequencies are sufficiently distant from that of the resonating nuclei in the same region that they are not excited by the first radiation), the spins of the unpaired electrons and the transition splitting nuclei can be decoupled by saturating the nmr transition of the transition splitting nuclei with a high intensity radiation at the Larmor frequency of the transition splitting nuclei. With such saturation, the hyperfine structure in the esr spectrum disappears to leave a single peak and the esr transition can readily be saturated using a single second radiation source as previously discussed. For this mode of operation, the ESREMRI apparatus should be provided with means for emitting the third radiation. The third radiation emission may be continuous or pulsed (or may take form of a continuous train on a series of trains of micropulses as described earlier for the second radiation) and suitably is emitted over substantially the same period as the second radiation.

The second radiation source(s) and, where present, the third radiation source will therefore, like the first radiation source, preferably be provided with means for adjusting pulse timing, pulse duration, central frequency, bandwidth and intensity if they are pulsed sources, and central frequency, bandwidth and intensity if they are CW emitters.

The sample may be exposed to the second radiation either continuously or for one or more periods between the initiating pulses of subsequent first radiation pulse sequences. Preferably, exposure to the second radiation will be in the period in which no field gradients are imposed on the sample, e.g. for at least part, and preferably all, of the delay period between the final FID signal detection period of each sequence and the initial first radiation pulse of the next.

Since ESREMRI permits images to be obtained with adequate resolution at lower than conventional main magnetic fields, the primary magnet in the ESREMRI apparatus may, if desired, be arranged for operation at low fields, e.g. 0.002 to 0.1 T, especially about 0.02 T, or even as low as the ambient magnetic field, i.e. about $5 \times 10^{-5}$ Tesla. Low field operation is particularly preferred not only for economic reasons but also to minimize MW heating of the subject and to improve tissue contrast which is generally found to increase with decreasing field strength.

The ESREMRI apparatus should particularly preferably be arranged for operation both with and without the amplified FID in order that conventional imaging may also be performed on the same apparatus.

The apparatus is arranged to allow ESREMRI of the sample to be performed and in certain instances may simply constitute a conventional MRI apparatus adapted by the provision of a second radiation source as described above. The MRI procedure involved in ESREMRI may also involve any one of the conventional image generation procedures, such as for example back projection or three- or two-dimensional Fourier transformation (3DFT and 2DFT), although the latter two of these may generally be preferred.

In 2DFT, the sample is placed in a magnetic field (the field direction being the Z direction) and is allowed to equilibrate. A small field gradient (the slice selection gradient) is then applied, e.g. in the Z direction, and while the slice selection gradient is superimposed on the main field the sample is exposed to an RF pulse (the initiating pulse) of a given central frequency, bandwidth and duration. Together, the central frequency, the bandwidth and the combination of the main field and the slice selection gradient serve to define the position and thickness of the image zone, the tomographic section through the sample transverse to the slice selection gradient in which the resonating nuclei will be excited by the RF pulse. The duration of the pulse determines the resultant change in transverse and longitudinal magnetization of the resonating nuclei. With a 90° pulse, after the slice selection gradient and the RF pulse are simultaneously terminated, a small field gradient (the phase encoding gradient) is then imposed for a short period in a direction transverse to the slice selection gradient, e.g. in the Y direction, causing the phase of the oscillating FID signal to become dependant on the position in the Y direction of the signal's source and thus encoding spatial information in the phase of the FID signal. After the phase encoding gradient is terminated, a third small field gradient (the read gradient) in a direction perpendicular to the previous two (the X direction) is imposed to encode spatial information in the FID frequency and the FID signal is detected and its intensity as a function of time is recorded during the imposition of the read gradient.

The FID signal that is detected is the combination of signals from resonating nuclei throughout the image zone. If in simple terms it is viewed as the sum of signals from an array of sources extending in the XY plane, the oscillating signal from each source will have an overall intensity dependent on the local density of the resonating nuclei, a frequency dependant on the position of the source in the X direction and a phase dependant on the position of the source in the Y direction.

The read gradient is terminated after the FID signal decays and, after a delay time to permit equilibration, the slice selection gradient is reimposed and the initiating RF pulse of the subsequent pulse sequence is applied.

Image generation requires detections of the FID signal for a series of pulse sequences, each with a phase encoding gradient of different strength or duration, and two-dimensional Fourier transformation of the resultant data can extract the spatial information to construct a two dimensional image, in the case described an SR image.

Different imaging techniques, such as IR, SE, etc., or different image generation techniques, e.g. simultaneous slice, volume acquisition, back projection etc., will of course require different pulse and field gradient imposition sequences, sequences which are conventional in the art.

The invention will now be described further by way of example and with reference to the accompanying drawings, in which:

FIG. 2 is a schematic perspective drawing of the emitters of the first and second radiation in the apparatus of FIG. 1.

Figure 1:
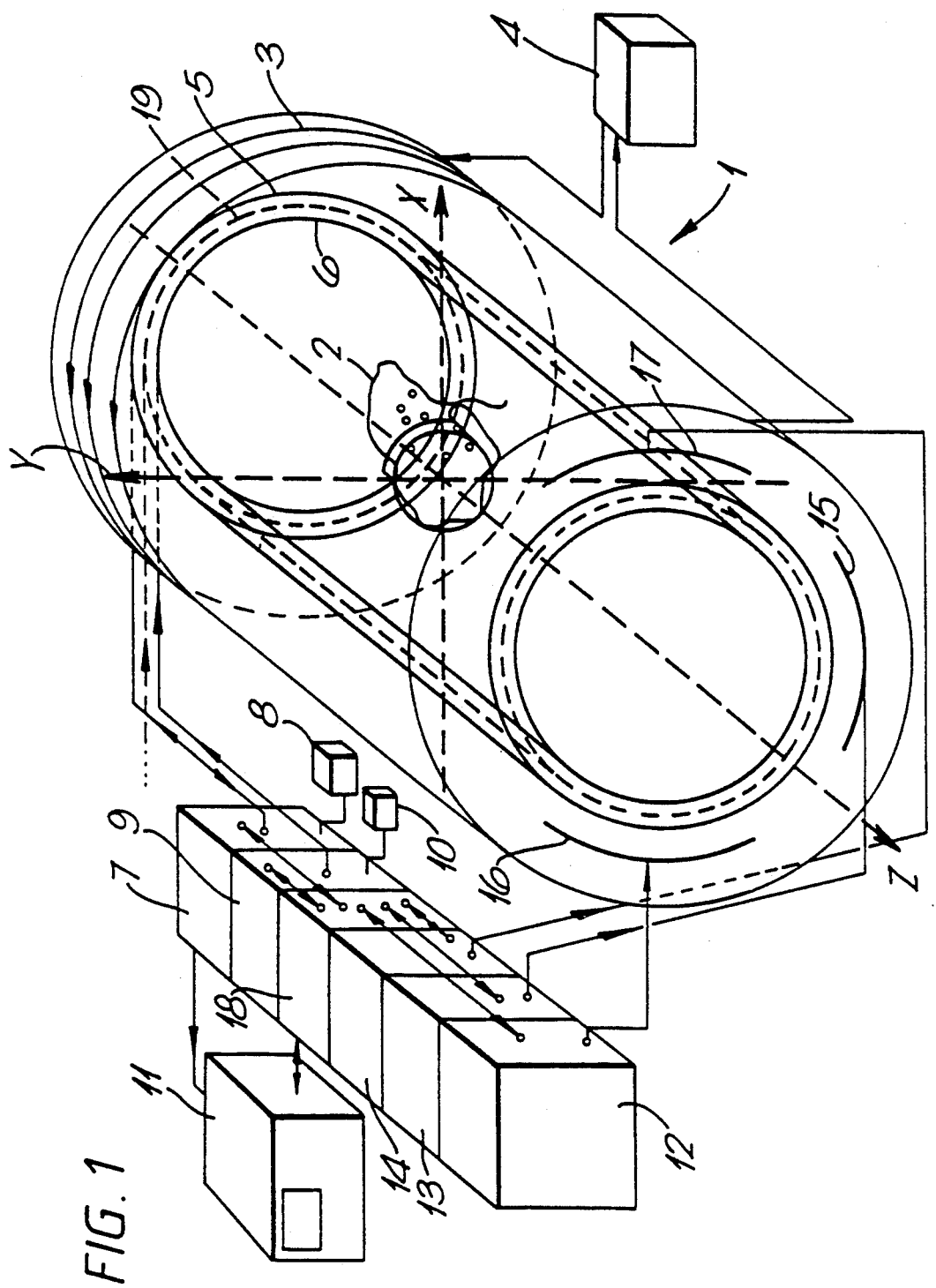
FIG. 1 is a schematic perspective drawing of an ESREMRI apparatus.

Referring to FIG. 1, there is shown an ESREMRI apparatus 1 having a sample 2, dosed with a paramagnetic contrast medium manufactured according to the invention, placed at the axis of the coils of electromagnet 3. Power from DC supply 4 to the electromagnet 3 enables the primary magnetic field, for example a 0.02 Tesla field, to be generated.

The apparatus is further provided with resonators 5 and 6 for emitting the first and second radiations respectively. Resonator 5 is connected to RF transceiver 7 powered by power supply 8 and resonator 6 is connected, for example by waveguides, to microwave generator 9 which is powered by power supply 10.

Microwave generator 9 may be arranged to emit MW radiation having more than one maximum frequency in order to excite more than one esr transition.

The frequency selection, bandwidth, pulse duration and pulse timing of the first and second radiations emitted by resonators 5 and 6 are controlled by control computer 11 and interface module 18.

Computer 11 also controls the power supply from power sources 12, 13 and 14 to the three pairs of Helmholtz coils 15, 16 and 17 which are shown in further detail in FIG. 2. The coils of coil pair 15 are coaxial with the coils of electromagnet 3 and the saddle coils of coil pairs 16 and 17 are arranged symmetrically about that axis, the Z axis, with their own axes mutually perpendicular and perpendicular to the Z axis. Coil pairs 15, 16 and 17 are used to generate the magnetic field gradients that are superimposed on the primary field at various stages of the imaging procedure, e.g. in two-dimensional Fourier transform imaging, and the timing sequence for operation of the coil pairs and for operation of the MW generator and the RF transceiver is controlled by computer 11 and interface module 18.

The apparatus may also be provided with decoupler comprising a further RF resonator 19 (shown with broken lines) connected to an RF transmitter and a power supply (not shown) and controlled by computer 11. The decoupler may be operated to emit a third radiation at a frequency selected excite the nuclear spin transition in non-zero spin nuclei in the contrast agent.

In operation in MRI, the power supply to the electromagnet 3 is switched on and the primary magnetic field is generated within the cavity within its coils. The magnitude of the primary field generated by electromagnet 3 is maintained essentially constant throughout the imaging procedure.

The sample 2, for example a patient, is placed within the coil cavity and after a short delay, for example several seconds, the imaging procedure can begin.

Interface module 18 activates the power supply to coil pair 15 for a short time period during which DC current flowing through the coils of coil pair 15 in opposite directions about the Z axis results in an approximately linear field gradient in the Z direction being imposed on the primary field.

within the time period for which coil pair 15 is energized, interface module 18 activates RF transceiver 7 to cause resonator 5 to emit an RF pulse, e.g. a 90° pulse, to excite the nmr transition of those resonating nuclei (generally protons) whose Larmor frequencies correspond to the frequency band of the RF pulse. The duration, intensity, band width and central frequency of the RF pulse may be selected by computer 11. For a given isotope in a given chemical environment, the major determining factor for the Larmor frequency will be the magnitude of the externally applied magnetic field, and thus effectively the RF pulse serves to excite the MR transition of the selected non-zero nuclear spin isotope (generally water protons) within a cross-section (the image zone) of the sample that is transverse to but has thickness in the Z direction.

On termination of the RF pulse, current in coil pair 15 is also terminated and after a very short delay interface module 18 energizes coil pair 16 to provide a field gradient in the Y direction for a short time period. This is termed the phase encoding gradient as the field gradient causes the Larmor frequency for the resonating nuclei to vary linearly across the image zone in the Y direction for the period that coil pair 15 is energized. With the removal of the perturbation of the Larmor frequencies on termination of the phase encoding gradient, the oscillation frequencies of the contributions to the FID signal from different source areas of the image zone return to being substantially the same, but the phases of such contributions are shifted to an extent dependant on the location of the particular source area along the Y direction.

After terminating current in coil pair 16, the interface module 18 then energizes coil pair 17 to provide a field gradient (the read gradient) in the X direction, and reactivates RF transceiver 7 to detect the FID signal from the sample.

The FID signal is assumed to arise from the transverse magnetization of the nuclear spin system within the image zone since the MR transition was excited by the RF pulse for resonating nuclei in this zone only. As described above, the intensity of the FID signal as a function of time contains encoded information regarding the distribution of the resonating nuclei in the image zone in the X and Y directions respectively.

The FID signal intensity falls off rapidly and exponentially with time as the system dephases and the period for which the read gradient is imposed and the transceiver 7 detects the FID signal from the sample is generally very short, for example of the order of milliseconds.

To generate an MR image of the image zone it is necessary to repeat the pulse and detection sequence for many further times, e.g. 64–1024 times, each time generating phase encoding gradients of different magnitude or duration. Often, to produce a good S/N ratio, signals for several, e.g. 2–4, identically performed sequences will be summed. FID signals for each set of sequences are transformed by the computer 11 using a standard two-dimensional Fourier transform algorithm to produce the desired spatial images of the image zone.

In conventional MRI, after termination of the only or the last FID signal detection period in a pulse and detection sequence and before the subsequent imposition of the slice selection gradient and emission of the initiating RF pulse of the next sequence, it has been necessary to wait for a delay period, generally of the order of seconds, until the resonating nuclei have relaxed to near equilibrium in order to build up sufficient longitudinal magnetization for the FID signal following the new RF pulse to be sufficiently strong to give an acceptable S/N ratio.

However, in ESREMRI, the delay period following the only or the last detection period may be reduced by the use of the amplified nuclear population difference resulting from the coupling between the electron MR and nuclear MR transitions. Alternatively put, amplified nuclear population difference, and thus contrast enhancement, may be obtained by MW stimulation of the sample before the or each RF pulse sequence. Thus for example in at least the period between termination of the last read gradient for each pulse sequence and the emission of the initiating RF pulse of the next sequence, for example for a period of about 10 ms to 100 ms, interface module 18 activates MW generator 9 to cause the sample to be irradiated with MW radiation of a central frequency corresponding to the Larmor frequency of the paramagnetic centre in the contrast agent in the sample, either CW radiation or, preferably, a train of radiation pulses.

The contrast enhancement in MRI achievable by the use of deuterated paramagnetic contrast agents and of MW stimulation of esr transitions of the contrast agents is illustrated by the results set forth in Table I below.

The table presents contrast enhancement values for test samples comprising tubes containing solutions of a range of varying concentrations of a range of deuterated stable free radicals in a range of solvents at a range of different MW power levels using a primary magnet of 0.02 T.

The contrast enhancement values are determined as the ratio of the "areas under the peaks" of the saturation recovery FID signals with and without imposition of the MW radiation.

The four solvents used were water, Seronorm, water having reduced dissolved oxygen ("Deoxy-$H_2O$") and Seronorm having reduced dissolved oxygen ("DeoxySeronorm"). Reduction of dissolved oxygen levels was achieved by bubbling nitrogen through water or Seronorm for about 1 minute. Seronorm is an artificial human serum available from Nycomed AS, Oslo, Norway.

| Compound | Power (W) | Concentration (mM) | Line-Width ($10^{-4}$ Tesla)* | $H_2O$ | Deoxy-$H_2O$ | Seronorm | Deoxy-Seronorm |
|---|---|---|---|---|---|---|---|
| 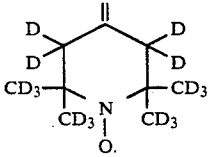 | 2 | 5 | 0.5(0.7)** | | | 36 | |
| 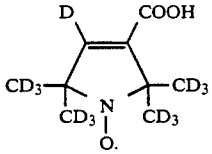 | 1 | 1.25 | 0.36 | 42.0 | | 27.5 | |
| | 1 | 2.5 | 0.24 | 50.6 | | 29.4 | |
| | 1 | 5 | 0.46 | 33.1 | 27.9 | 22.7 | 21.1 |
| | 2 | 1.25 | 0.36 | 55.8 | | 37.4 | |
| | 2 | 2.5 | 0.24 | 76.6 | | 44.7 | |
| | 2 | 5 | 0.46(0.87) | 62.1 | 49 | 40.5 | 37.0 |
| | 20 | 5 | | | 137 | | 80.7 |
| 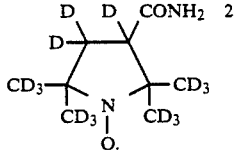 | 2 | 5 | 0.67(0.9) | 55 | 85.9 | 33.7 | 51.2 |
| 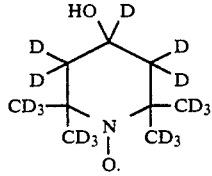 | 2 | 5 | 0.63 | 62.5 | 99.1 | 36.9 | 53.0 |

-continued

| Compound | Power (W) | Concentration (mM) | Line-Width ($10^{-4}$ Tesla)* | Contrast Enhancement in | | | |
|---|---|---|---|---|---|---|---|
| | | | | $H_2O$ | Deoxy-$H_2O$ | Seronorm | Deoxy-Seronorm |
| 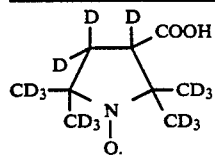 | 2 | 5 | 0.52(0.87) | 64.2 | 86.0 | 60.3 | 59.9 |

*values in brackets for fully protonated analogues
**protonated value is for 5.5 mM concentration All these compounds are commercially available or are preparable using the methods described in the literature mentioned herein.

I claim:

1. A method of generating a magnetic resonance image of a sample, said method comprising introducing into said sample a physiologically tolerable deuterated stable free radical having an electron spin resonance transition having a linewidth of 1 Gauss or less, exposing said sample to first and second radiations of frequencies selected respectively to excite nuclear spin transitions in selected nuclei in said sample and to excite electron spin resonance transitions of said free radical coupled to nuclear spin transitions of at least some of said nuclei, detecting magnetic resonance signals from said sample, and generating a magnetic resonance image from said signals.

2. A method as claimed in claim 1 wherein said deuterated radical is administered into said sample at a concentration from 0.1 to 1000 mM.

3. A method as claimed in claim 1 wherein magnetic resonance imaging is carried out at a primary field strength of $5 \times 10^{-5}$ to 0.1 Tesla.

* * * * *